(12) United States Patent
Choi et al.

(10) Patent No.: US 9,433,641 B2
(45) Date of Patent: *Sep. 6, 2016

(54) SKIN EXTERNAL COMPOSITION COMPRISING A SALT AND SUGAR AS ACTIVE INGREDIENTS FOR PREVENTING AND TREATING VAGINOSIS AND THE USE THEREOF

(71) Applicants: Won Seog Choi, Jeonju-si (KR); Dong-Yeul Kwon, Daejeon (KR)

(72) Inventors: Won Seog Choi, Jeonju-si (KR); Dong-Yeul Kwon, Daejeon (KR)

(73) Assignee: Won Seog Choi, Jeonju-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/450,637

(22) Filed: Aug. 4, 2014

(65) Prior Publication Data

US 2014/0377375 A1 Dec. 25, 2014

Related U.S. Application Data

(63) Continuation-in-part of application No. 13/501,910, filed as application No. PCT/KR2010/007068 on Oct. 15, 2010, now abandoned, said application No. 14/450,637 is a continuation-in-part of application No. 14/025,698, filed on Sep. 12, 2013, now abandoned, which is a continuation-in-part of application No. 14/025,654, filed on Sep. 12, 2013, which is a continuation-in-part of application No. 13/501,910, filed on Apr. 13, 2012, now abandoned.

(30) Foreign Application Priority Data

Oct. 19, 2009 (KR) .................. 10-2009-0099333
Oct. 7, 2010 (KR) .................. 10-2010-0097774

(51) Int. Cl.

| | | |
|---|---|---|
| *A61K 33/14* | (2006.01) |
| *A61K 47/26* | (2006.01) |
| *A61K 31/7016* | (2006.01) |
| *A61K 31/7004* | (2006.01) |
| *A61K 33/20* | (2006.01) |
| *A61K 8/60* | (2006.01) |
| *A61K 8/19* | (2006.01) |
| *A61K 9/20* | (2006.01) |
| *A61K 9/00* | (2006.01) |
| *A61Q 19/00* | (2006.01) |
| *A61K 8/96* | (2006.01) |

(52) U.S. Cl.
CPC .............. *A61K 33/14* (2013.01); *A61K 8/19* (2013.01); *A61K 8/60* (2013.01); *A61K 8/965* (2013.01); *A61K 9/0034* (2013.01); *A61K 9/2013* (2013.01); *A61K 31/7004* (2013.01); *A61K 33/20* (2013.01); *A61K 47/26* (2013.01); *A61Q 19/005* (2013.01); *A61K 9/2009* (2013.01); *A61K 9/2018* (2013.01)

(58) Field of Classification Search
CPC .. A61K 31/7004; A61K 33/14; A61K 33/20; A61K 8/19; A61K 8/60; A61K 9/0034; A61K 9/2009; A61K 9/2013; A61K 9/2018; A61Q 19/005

See application file for complete search history.

(56) References Cited

U.S. PATENT DOCUMENTS

| | | | |
|---|---|---|---|
| 2006/0105963 A1 | 5/2006 | Yang et al. | |
| 2009/0232939 A1 | 9/2009 | Berge | |
| 2012/0201904 A1* | 8/2012 | Choi | A61K 9/0034 424/680 |

FOREIGN PATENT DOCUMENTS

| | | |
|---|---|---|
| KR | 2001-0029068 A | 4/2001 |
| WO | 97/43989 | 11/1997 |

OTHER PUBLICATIONS

Tan, Man Minh et al., 2012, Feasibility of Laser-Induced Breakdown Spectroscopy (LIBS) for Classification of Sea Salts, Applied Spectroscopy, vol. 66, No. 3, 262-271.
Kim, Hack-Youn et al., 2010, Effect of bamboo salt on the physicochemical properties of meat emulsion systems, Meat Science, 86, 96-965.
Srinivasan, S., and D.N. Fredricks, The Human vaginal Bacterial Biota and Bacterial vaginosis, Interdisciplinary Perspectives on Infectious Diseases, vol. 2008, Article ID 750479, 1-22.
Choi, Jang-Gi et al., 2010, Antibacterial Activity of Eckonia cava Against Methicillin-Resistant *Staphylococcus aureus* and *Salmonella* spp., vol. 7, No. 4, 435-441.
Choi, Jang-Gi et al., 2010, Antibacterial Activity of Hylomecon hylomeconoidea Against Methicllin-Resistant *Staphylococcus aureus*, Appl. Biochem. Biotechnol., 160, 8, 2467-2474.
Hahn, Seokyung et al., 2001, Reduced osmolarity oral rehydration solution for treating dehydration due to diarrhoea in children: systemic, British Medical Journal, vol. 323, 81-85.

* cited by examiner

*Primary Examiner* — Rachael E Bredefeld
(74) *Attorney, Agent, or Firm* — Kirk Hahn

(57) ABSTRACT

A skin external composition comprising a combination of salt and sugar as an active ingredient in an amount effective to treat and prevent vaginosis, together with a pharmaceutically acceptable carrier, and the use thereof.

24 Claims, No Drawings

SKIN EXTERNAL COMPOSITION COMPRISING A SALT AND SUGAR AS ACTIVE INGREDIENTS FOR PREVENTING AND TREATING VAGINOSIS AND THE USE THEREOF

CROSS-REFERENCE TO RELATED APPLICATIONS

This application is a Continuation-in-Part of U.S. National Phase patent application Ser. No. 13/501,910, filed on Apr. 13, 2012, which claims priority to PCT Patent Application No. PCT/KR2010/007068, filed on Oct. 15, 2010, Korean Patent Application No. 10-2010-0097774, filed on Oct. 7, 2010 and Korean Patent Application No. 10-2009-0099333, filed on Oct. 19, 2009; the contents of which are all herein incorporated by this reference in their entireties. Additionally, this application is a Continuation-in-Part of U.S. Non-Provisional patent application Ser. No. 14/025,698, filed on Sep. 12, 2013, which is a Divisional of U.S. National Phase patent application Ser. No. 13/501,910, filed on Apr. 13, 2012, which claims priority to PCT Patent Application No. PCT/KR2010/007068, filed on Oct. 15, 2010, Korean Patent Application No. 10-2010-0097774, filed on Oct. 7, 2010 and Korean Patent Application No. 10-2009-0099333, filed on Oct. 19, 2009; the contents of which are all herein incorporated by this reference in their entireties. Additionally, this application is a Continuation-in-Part of U.S. Non-Provisional patent application Ser. No. 14/025,654, filed on Sep. 12, 2013, which is a Continuation-in-Part of U.S. National Phase patent application Ser. No. 13/501,910, filed on Apr. 13, 2012, which claims priority to PCT Patent Application No. PCT/KR2010/007068, filed on Oct. 15, 2010, Korean Patent Application No. 10-2010-0097774, filed on Oct. 7, 2010 and Korean Patent Application No. 10-2009-0099333, filed on Oct. 19, 2009; the contents of which are all herein incorporated by this reference in their entireties. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

BACKGROUND OF THE INVENTION

The present application relates to an external skin composition comprising a salt and a sugar as active ingredients for preventing and treating vaginosis and the use thereof.

Vaginitis is a condition that occurs especially during pregnancy in the vagina causing vaginal discharge, inflammation, and irritation, as well as, vulvar or vaginal itching. The three most common vaginal infections and diseases are also the most frequent causes of vaginitis. The three common vaginal infections include: bacterial vaginosis, vaginal yeast infection, and trichomoniasis.

The human vagina is colonized with various microbes, yeasts and germs, for example, about more than $10^4$ numbers/ml (vaginal fluid) of Lactobacillus spp. such as, Lactobacillus crispatus and Lactobacillus jensenii, which provide a weak acidic environment ranging from pH 4.5-5.1 to protect from a microbial infection. Additionally, the vagina is a highly versatile organ that can profoundly affect the health of women and their newborn infants. It has been reported that there are many important pathogens in the vaginal niche, such as, Neiserria gonorrhea, Ureaplasma species, Mycoplasma genitalium, Streptococcus species, Escherichia coli, Chlamydia trachomatis, and Trichomonas vaginalis, etc.

Bacterial vaginosis (BV), the most prevalent and detrimental vaginosis, gives rise to malodorous vaginal discharge or local irritation of the woman with BV and is associated with several more serious adverse outcomes including pre-term birth, pelvic inflammatory disease, and acquisition of HIV infection. Women with bacterial vaginosis (BV) have lost many Lactobacillus species (except L. iners) and have acquired a variety of anaerobic and facultative bacteria. Gram stains of vaginal fluid from women with BV show a loss of Gram-positive rods and their replacement with Gram-negative and Gram-variable cocci and rods. Cultures of vaginal fluid from subjects with BV typically yield Gardnerella vaginalis and a mixture of other bacteria that may include Peptosterptococcus, Mobiluncus, Bacterioides, Prevotella, Porphyromonas, Mobiluncus and Mycoplasma species. (Sujatha Srinivasan and David N. Fedricks, Review Article, The Human Vaginal Bacterial Biota and Bacterial Vaginosis, Interdisciplinary Perspectives on Infectious Diseases, Vol., 2008, Article ID 750479, pp 1-3).

There have been studies to develop effective therapies to treat vaginitis, for example, orally administrated broad spectrum antibiotics, such as, metronidazole. However, this therapy has many disadvantages, such as, antibiotic intolerance, systemic toxicity in case of long-term administration, and a probable destruction of the normal bacterial flora in the vagina. These treatments cause secondary complications, such as, a decreased number of Lactobacillus spp., an increase of vaginal pH, and a proliferation of anaerobic microbes.

Accordingly, there is a need to develop novel therapeutic compositions showing treatments with long-term activity and safety to treat vaginosis.

However, there has never been a treatment reported or disclosed on the use of a composition with a combination of salt and sugar with a therapeutic effect on vaginosis. None of the above cited references, which are incorporated herein by reference, disclose a treatment using a combination of salt and sugar.

The applicants have carried out antibacterial test, especially Gardnerella vaginalis, a main cause of vaginosis, to investigate the inhibitory effect of a combination of salt and sugar on vaginosis. The results of these tests confirmed that a combination of salt and sugar showed potent antibacterial activity.

These results and other disclosures will become apparent from the detailed disclosure of the discoveries provided hereinafter.

BRIEF SUMMARY OF INVENTION

Accordingly, an embodiment of the present disclosure is an external skin composition comprising a combination of salt and sugar as an active ingredient in an amount effective to treat or prevent vaginosis, together with a pharmaceutically acceptable carrier.

Another embodiment of the present disclosure is a use of a combination of salt and sugar in the manufacture of a medicament employed for treating or preventing vaginosis in a mammal.

Another embodiment of the present disclosure is a method of treating or preventing vaginosis in a mammal wherein the method comprises administering to said mammal an effective amount of a combination of salt and sugar, together with a pharmaceutically acceptable carrier thereof.

DETAILED DESCRIPTION OF THE INVENTION

One embodiment of the present disclosure is an external skin composition comprising a combination of salt and sugar as an active ingredient in an amount effective to treat or prevent vaginosis, together with a pharmaceutically acceptable carrier.

Another embodiment of the present disclosure is a use of a combination of salt and sugar in the manufacture of a medicament employed for treating or preventing vaginosis in a mammal.

Another embodiment of the present disclosure is a method of treating or preventing vaginosis in a mammal wherein the method comprises administering to said mammal an effective amount of a combination of salt and sugar together with a pharmaceutically acceptable carrier thereof.

The term, "salt" defined herein comprises natural salts (unrefined salt from sea or brine ponds and mined mineral salt) or processed salts (refined salts to eliminate trace compounds and/or to add compounds (e.g., fluoride). Sea salts from Korea and other coastal countries are especially good for the disclosed purpose of treating vaginosis in a mammal. Also, included in the definition of "salt" are a pure salt, sodium chloride, melted salt [also called molten salt], or melted [molten] natural salt. Melted [molten] salt is a salt which is solid at standard temperature and pressure (STP) but enters the liquid phase when heated. Melted [molten] salt is prepared by melting the salt at a temperature ranging from 200 to 2000° C., or commonly from 800 to 1200° C., for a period ranging from 2 hours to 7 days or commonly 12 hours to 48 hours.

Sea salt is salt produced from the evaporation of seawater. The colors and variety of flavors are due to local clays and algae found in the waters the salt is harvested from. For example, some boutique salts from Korea and France are pinkish gray, some from India are black.

The chemical composition of sea salt is typically the same as the ions dissolved in seawater. By dry weight percent: Sodium, 30.8; Potassium, 1.1; Magnesium, 3.7; Calcium, 1.2; Chloride, 55.5; Sulfate, 7.7. However, a study found the amount of trace elements, such as titanium, silver, cobalt, and lead in synthetic sea salt are much higher than those in sea water. The magnitude of the difference can be as large as $10^4$ times.

Unrefined sea salt contains small amounts of magnesium and calcium halides and sulphates, traces of algal products, salt-resistant bacteria and sediment particles. The calcium and magnesium salts confer a faintly bitter overtone, and they make unrefined sea salt hygroscopic (i.e., it gradually absorbs moisture from air if stored uncovered). Algal products contribute a mild "sea-air" smell, the latter from organobromine compounds. Sediments, the proportion of which varies with the source, give the salt a dull grey appearance.

The mineral content also affects the taste. Taste and aroma compounds are often detectable by humans in minute concentrations; sea salt may have a more complex flavor than pure sodium chloride.

Different natural salts have different mineralities depending on their source, giving each one a unique flavor. Fleur de sel, a natural sea salt from the surface of evaporating brine in salt pans, has a unique flavor varying with the region from which it is produced.

In traditional Korean cuisine, so-called "bamboo salt" is prepared by roasting salt at temperatures between 800 and 2000° C. in a bamboo container plugged with mud at both ends. This product absorbs minerals from the bamboo and the mud.

Melted Salt originates from Korea. It was originally developed by Korean doctors and monks almost 1,000 years ago as a folk medicinal remedy for various illnesses. The Melted Salt was originally made by putting sea salt into cases made from bamboo trunks.

After the salt was inserted into the trunks, the ends were sealed with natural yellow clay that was rich in minerals. The trunks were then roasted in a furnace. The process required 10 hours of roasting at a temperature between 1,000° to 1,500° C. This procedure could be repeated from three to nine times.

Through repeated experimentations, doctors discovered that Melted Salt gained higher medical effectiveness if it was baked for more time. This method enhanced the amalgamation of minerals from the yellow clay into the sea salt.

Additionally, the numerous high-heat roasting process was more effective in ridding of impurities in the sea salt.

It has been found that the salt reaches its highest medical efficacy when it is baked for 9 times. Melted Salt is labeled as 1×, 3×, 6×, 9× indicating the number of roasting processes the specific Melted Salt has received. Because the medical efficacy correlates with the amount of roasting procedures, the price range can differ significantly depending on the number of roasting processes.

Melted Salt contains many minerals due to the leaching of minerals. The main components of Melted Salt are calcium, phosphorus, magnesium, iron, manganese, copper, potassium, and zinc. Melted Salt is highly alkaline in contrast to other salts which are acidic. This also makes Melted Salt a great neutralizer.

Sea salt tends to be coarser than table salt. Unrefined sea salt is found to have many minerals that regular table salt lacks such as potassium, magnesium, calcium, and iodine. Because of this, a lot of people use sea salts instead of table salts.

Salts, in general, can suppress fungal and bacterial growth. Melted Salt excels in comparison to other salts. As a matter of fact, it has been shown in clinical studies that Melted Salt can actually prevent *Salmonella* infection.

Melted Salt, unlike other salts that are acidic, is highly alkaline (pH of 10.5) because of the high sulfur content. Therefore, it can act as a neutralizer for acidic food. Also because of this unique property, the iron in Melted Salt does not oxidize like the iron in other salts. Melted Salt produces reduction reactions. It suppresses inflammations and slows down cell proliferation.

The most salt is made by evaporating water from a brine and is positively charged. However, since Melted Salt is made by melting salt at a high temperature and then cooling to a solid, it is negatively charged.

The term, "sugar" defined herein comprises a saccharide compound: mono-saccharides, such as, glucose, fructose, mannose, galactose, etc. and disaccharides, such as, lactose, maltose, sugar, etc. Glucose or crystalline glucose show good results when used in compositions to treat vaginosis.

The term, "a combination of salt and sugar" defined herein comprise a combination of salt and sugar mixed at a ration in a composition. One embodiment of the ratio is a salt:sugar ratio of 1:1-30 (w/w). Another embodiment of the ratio is a salt:sugar ratio of 1:1-10 (w/w). Another embodiment of the ratio is a salt:sugar ratio of 1:1-5 (w/w). Another embodiment of the ratio is a salt:sugar ratio of 1:1-3 (w/w).

Therefore, the amount of sugar is equal to or up to 30 times greater than the amount of salt.

The term, "vaginosis" defined herein comprises a vaginosis selected from bacterial vaginosis, especially *Gardnerella vaginalis*; fungal vaginitis and *Tricomonas vaginitis*.

The composition of the present disclosure may further contain other ingredients, i.e., antibiotics, dyes, and flavors, in an amount from about 0.1 to about 20% by weight of the above composition based on the total weight of the composition. If the composition contains other ingredients, the quantity of sugar and salt is in an amount from about 99.9% to about 80% by weight.

Hereinafter, the present disclosure is described in detail.

A composition of the disclosure comprising the combination of salt and sugar can be prepared in detail by following procedures, For example, a cleansing combination of the present disclosure can be prepared as follows: a natural salt or processed salt is melted at a temperature ranging from 200 to 2000° C. for the period ranging from 2 hours to 7 days to obtain the melted salt of the first step. The melted salt is mixed with a sugar compound with a salt:sugar ratio of 1:1-30 (w/w) to obtain the disclosed combination. Then the combination is dissolved in an appropriate amount of distilled water, buffer, or isotonic solution with an appropriate amount of other additives (if needed), such as, the antibiotics, dyes, or flavors to obtain the cleansing composition.

It have been proven that the composition comprising a combination of salt and sugar prepared by the above-described method showed potent antibacterial activity, especially against *Gardnerella vaginalis*, a main cause of vaginosis, as well as, stimulating the production of lactic acid to maintain the vagina acidity by way of stimulating the proliferation of *Lactobacillus acidophilus*.

Accordingly, external skin composition is disclosed comprising a combination of salt and sugar prepared by the above-described method for treating or preventing vaginosis, together with a pharmaceutically acceptable carrier.

Additionally, the present application discloses a use of a combination of salt and sugar prepared by the above-described method in the manufacture of a medicament employed for treating or preventing vaginosis disease in a mammal.

Additionally, the present application discloses a method of treating or preventing vaginosis disease in a mammal wherein the method comprises administering to said mammal an effective amount of a combination of salt and sugar prepared by the above-described method, together with a pharmaceutically acceptable carrier thereof.

The term "prevent" defined herein means the inhibition of diseases in a mammal which is prone to catch these diseases and the term "treat" used herein means (a) the inhibition of the development of disease or illness; (b) the alleviation of disease or illness; or (c) the elimination of disease or illness.

The disclosed composition may additionally comprise conventional carrier, adjuvants or diluents in accordance with using the method. It is suggested that the carrier used be an appropriate substance according to the usage and application method, but it is not limited. Appropriate diluents are listed in the written text of Remington's Pharmaceutical Science (Mack Publishing Co, Easton Pa.).

Hereinafter, the following formulation methods and excipients are merely exemplary and in no way limit the disclosure.

The composition according to the present disclosure can be provided as an external skin composition containing pharmaceutically acceptable carriers, adjuvants or diluents, e.g., lactose, dextrose, sucrose, sorbitol, mannitol, xylitol, erythritol, maltitol, starches, acacia rubber, alginate, gelatin, calcium phosphate, calcium silicate, cellulose, methyl cellulose, polyvinyl pyrrolidone, water, methylhydroxy benzoate, propylhydroxy benzoate, talc, magnesium stearate and mineral oil. The formulations may additionally include fillers, anti-agglutinating agents, lubricating agents, wetting agents, flavoring agents, emulsifiers, preservatives and the like. The compositions of the present disclosure may be formulated so as to provide quick, sustained or delayed release of the active ingredient after their administration to a patient by employing any of the procedures well known in the art.

For example, the compositions of the present disclosure can be dissolved in distilled water, pH buffer, oils, propylene glycol or other solvents that are commonly used in the art. Suitable examples of the carriers include physiological saline, polyethylene glycol, ethanol, vegetable oils, isopropyl myristate, etc., but are not limited to them. For topical administration, the compounds of the present disclosure can be formulated in the form of ointments and creams.

The external skin composition of the present disclosure may be prepared in any form, for example, topical preparation such as cleansing liquid, gel, jelly, foam, cream, ointment, lotion, balm, patch, paste, spray solution, aerosol and the like, or insert preparation such as vaginal tablet, vaginal capsule, vaginal film, vaginal sponge, tampon, pad etc, preferably, vaginal tablet composition or cleansing liquid composition.

Accordingly, the present disclosure provides a cleansing liquid solution or vaginal tablet composition comprising a combination of salt and sugar for treating or preventing vaginosis, together with a pharmaceutically acceptable carrier.

The composition of the present disclosure in pharmaceutical dosage forms may be used in the form of their pharmaceutically acceptable salts, and also may be used alone or in appropriate association, as well as, in combination with other pharmaceutically active compounds, such as, antibacterial compounds or extracts derived from plants, animals or minerals well-known in the art.

The desirable dose of the present disclosure varies depending on the condition and the weight of the subject, severity, drug form, route and period of administration, and may be chosen by those skilled in the art. However, in order to obtain desirable effects, it is generally recommended to administer at the amount ranging from 0.001 mg/kg to 1000 mg/kg or an amount ranging from 0.01 mg/kg to 100 mg/kg by weight of the patient per day of the combination of the present disclosure. The dose may be administered in single or divided into several times per day.

In terms of composition, in one embodiment, the disclosed combination is between 0.01% to 99.99% by weight based on the total weight of the composition. In another embodiment, the disclosed combination is between 0.1% to 99% by weight based on the total weight of the composition. In another embodiment, the disclosed combination is between 1% to 20% by weight based on the total weight of the composition. In another embodiment, the disclosed combination is between 5% to 10% by weight based on the total weight of the composition.

The composition of the present disclosure can be administered to a subject animal, such as, mammals (rat, mouse, domestic animals or human) via various routes. All modes of administration are contemplated; for example, administration can be made externally, topically, orally, rectally or by intravenous, intramuscular, subcutaneous, intracutaneous, intrathecal, epidural or intracerebroventricular injection.

Additional embodiments are described in the following paragraphs.

Paragraph 1. A composition comprising: a melted salt and a sugar; wherein the melted salt and sugar have a mixed weight ratio from 1:1 to 1:30, wherein the weight of the sugar is equal to or greater than the weight of any other ingredient in the composition and wherein the total weight of the sugar and the melted salt is from 80% to 100% of the total weight of the composition.

Paragraph 2. The composition of Paragraph 1 wherein the melted salt is a melted sea salt.

Paragraph 3. The composition of Paragraph 1 wherein the melted sea salt is melted sodium chloride.

Paragraph 4. The composition of Paragraph 1, wherein the sugar is glucose.

Paragraph 5. The composition of Paragraph 1 wherein composition is a topical preparation selected from the group consisting of a cleansing liquid, gel, jelly, foam, cream, ointment, lotion, balm, patch, paste, spray solution, and aerosol.

Paragraph 6. The composition of Paragraph 5 wherein the composition is a cleansing liquid.

Paragraph 7. The composition of Paragraph 1 wherein composition is an insert preparation selected from the group consisting of tablet, capsule, film, sponge, tampon and pad.

Paragraph 8. The composition of Paragraph 7 wherein the composition is a tablet.

Paragraph 9. The composition of Paragraph 1, further comprising dissolving the composition in a liquid at a percentage of the composition to the liquid from 0.01% to 99.99%.

Paragraph 10. The composition of Paragraph 9, wherein the percentage of the composition to the liquid is from 5% to 10%.

Paragraph 11. The composition of Paragraph 9, wherein the liquid is selected from the group consisting of distilled water, a buffered solution, an isotonic solution, a physiological saline, an oil, propylene glycol, ethanol and isopropyl myristate.

Paragraph 12. A method of treatment comprising a) administering to a mammal the composition of Paragraph 1; and b) placing the composition in a vagina of the mammal in need of treatment for a bacterial vaginosis infection, wherein the bacterial vaginosis infection is a *Gardnerella vaginalis* infection.

Paragraph 13. The method of Paragraph 12, wherein the treatment is selected from the group consisting of inhibition of development of the *Gardnerella vaginalis* infection, alleviation of the *Gardnerella vaginalis* infection and elimination of the *Gardnerella vaginalis* infection.

Paragraph 14. The method of Paragraph 12, wherein administering to the mammal comprises administering an amount of the composition in Paragraph 1 ranging from 0.001 mg to 1000 mg per kilogram of body weight of the mammal.

Paragraph 15. The method of Paragraph 14, wherein the amount of the composition in Paragraph 1 ranges from 0.01 mg to 100 mg per kilogram of body weight of the mammal.

Paragraph 16. The method of Paragraph 12, wherein the composition is administered from once a day to several times per day.

Paragraph 17. A composition comprising: a sea salt and a sugar; wherein the sea salt and sugar have a mixed weight ratio from 1:1 to 1:30, wherein the weight of the sugar is equal to or greater than the weight of any other ingredient in the composition and wherein the total weight of the sugar and the sea salt is from 80% to 100% of the total weight of the composition.

Paragraph 18. The composition of Paragraph 17 wherein the sea salt is sodium chloride.

Paragraph 19. The composition of Paragraph 17, wherein the sugar is glucose.

Paragraph 20. The composition of Paragraph 17 wherein composition is a topical preparation selected from the group consisting of a cleansing liquid, gel, jelly, foam, cream, ointment, lotion, balm, patch, paste, spray solution, and aerosol.

Paragraph 21. The composition of Paragraph 20 wherein the composition is a cleansing liquid.

Paragraph 22. The composition of Paragraph 17 wherein composition is an insert preparation selected from the group consisting of tablet, capsule, film, sponge, tampon and pad.

Paragraph 23. The composition of Paragraph 22 wherein the composition is a tablet.

Paragraph 24. The composition of Paragraph 17, further comprising dissolving the composition in a liquid at a percentage of the composition to the liquid from 0.01% to 99.99%.

Paragraph 25. The composition of Paragraph 24, wherein the percentage of the composition to the liquid is from 5% to 10%.

Paragraph 26. The composition of Paragraph 24, wherein the liquid is selected from the group consisting of distilled water, a buffered solution, an isotonic solution, a physiological saline, an oil, propylene glycol, ethanol and isopropyl myristate.

Paragraph 27. A method of treatment comprising a) administering to a mammal the composition of Paragraph 17; and b) placing the composition in a vagina of the mammal in need of treatment for a bacterial vaginosis infection, wherein the bacterial vaginosis infection is a *Gardnerella vaginalis* infection.

Paragraph 28. The method of Paragraph 27, wherein the treatment is selected from the group consisting of inhibition of development of the *Gardnerella vaginalis* infection, alleviation of the *Gardnerella vaginalis* infection and elimination of the *Gardnerella vaginalis* infection.

Paragraph 29. The method of Paragraph 27, wherein administering to the mammal comprises administering an amount of the composition in Paragraph 1 ranging from 0.001 mg to 1000 mg per kilogram of body weight of the mammal.

Paragraph 30. The method of Paragraph 29, wherein the amount of the composition in Paragraph 1 ranges from 0.01 mg to 100 mg per kilogram of body weight of the mammal.

Paragraph 31. The method of Paragraph 27, wherein the composition is administered from once a day to several times per day.

Paragraph 32. A composition comprising: a combination of sodium chloride and glucose at a mixed weight ratio from 1:1 to 1:30, wherein the weight of the glucose is equal to or greater than the weight of any other ingredient in the composition and wherein the total weight of the glucose and the sodium chloride is from 80% to 100% of the total weight of the composition.

Paragraph 33. The composition of Paragraph 32 wherein composition is a topical preparation selected from the group consisting of a cleansing liquid, gel, jelly, foam, cream, ointment, lotion, balm, patch, paste, spray solution, and aerosol.

Paragraph 34. The composition of Paragraph 33 wherein the composition is a cleansing liquid.

Paragraph 35. The composition of Paragraph 32 wherein composition is an insert preparation selected from the group consisting of tablet, capsule, film, sponge, tampon and pad.

Paragraph 36. The composition of Paragraph 35 wherein the composition is a tablet.

Paragraph 37. The composition of Paragraph 32, further comprising dissolving the composition in a liquid at a percentage of the composition to the liquid from 0.01% to 99.99%.

Paragraph 38. The composition of Paragraph 37, wherein the percentage of the composition to the liquid is from 5% to 10%.

Paragraph 39. The composition of Paragraph 37, wherein the liquid is selected from the group consisting of distilled water, a buffered solution, an isotonic solution, a physiological saline, an oil, propylene glycol, ethanol and isopropyl myristate.

Paragraph 40. A method of treatment comprising a) administering to a mammal the composition of Paragraph 32; and b) placing the composition in a vagina of the mammal in need of treatment for a bacterial vaginosis infection, wherein the bacterial vaginosis infection is a *Gardnerella vaginalis* infection.

Paragraph 41. The method of Paragraph 40, wherein the treatment is selected from the group consisting of inhibition of development of the *Gardnerella vaginalis* infection, alleviation of the *Gardnerella vaginalis* infection and elimination of the *Gardnerella vaginalis* infection.

Paragraph 42. The method of Paragraph 40, wherein administering to the mammal comprises administering an amount of the composition in Paragraph 1 ranging from 0.001 mg to 1000 mg per kilogram of body weight of the mammal.

Paragraph 43. The method of Paragraph 42, wherein the amount of the composition in Paragraph 1 ranges from 0.01 mg to 100 mg per kilogram of body weight of the mammal.

Paragraph 44. The method of Paragraph 40, wherein the composition is administered from once a day to several times per day.

Paragraph 45. A composition comprising: a melted salt and a sugar; wherein the melted salt and sugar have a mixed weight ratio from 1:1 to 1:30, wherein the weight of the sugar is equal to or greater than the weight of any other ingredient in the composition and wherein the total weight of the sugar and the melted salt is from 30% to 100% of the total weight of the composition.

Paragraph 46. The composition of Paragraph 45, wherein the total weight of the sugar and the melted salt is from 50% to 100% of the total weight of the composition Paragraph 47. The composition of Paragraph 45, wherein the melted salt is a melted sea salt.

Paragraph 48. The composition of Paragraph 45, wherein the melted sea salt is melted sodium chloride.

Paragraph 49. The composition of Paragraph 45, wherein the sugar is glucose.

Paragraph 50. The composition of Paragraph 45, wherein composition is a topical preparation selected from the group consisting of a cleansing liquid, gel, jelly, foam, cream, ointment, lotion, balm, patch, paste, spray solution, and aerosol.

Paragraph 51. The composition of Paragraph 50, wherein the composition is a cleansing liquid.

Paragraph 52. The composition of Paragraph 45, wherein composition is an insert preparation selected from the group consisting of tablet, capsule, film, sponge, tampon and pad.

Paragraph 53. The composition of Paragraph 52, wherein the composition is a tablet.

Paragraph 54. The composition of Paragraph 45, further comprising dissolving the composition in a liquid at a percentage of the composition to the liquid from 0.01% to 99.99%.

Paragraph 55. The composition of Paragraph 54, wherein the percentage of the composition to the liquid is from 5% to 10%.

Paragraph 56. The composition of Paragraph 54, wherein the liquid is selected from the group consisting of distilled water, a buffered solution, an isotonic solution, a physiological saline, an oil, propylene glycol, ethanol and isopropyl myristate.

Paragraph 57. A method of treatment comprising a) administering to a mammal the composition of Paragraph 45; and b) placing the composition in a vagina of the mammal in need of treatment for a bacterial vaginosis infection, wherein the bacterial vaginosis infection is a *Gardnerella vaginalis* infection.

Paragraph 58. The method of Paragraph 57, wherein the treatment is selected from the group consisting of inhibition of development of the *Gardnerella vaginalis* infection, alleviation of the *Gardnerella vaginalis* infection and elimination of the *Gardnerella vaginalis* infection.

Paragraph 59. The method of Paragraph 57, wherein administering to the mammal comprises administering an amount of the composition in Paragraph 45 ranging from 0.001 mg to 1000 mg per kilogram of body weight of the mammal.

Paragraph 60. The method of Paragraph 59, wherein the amount of the composition in Paragraph 1 ranges from 0.01 mg to 100 mg per kilogram of body weight of the mammal.

Paragraph 61. The method of Paragraph 57, wherein the composition is administered from once a day to several times per day.

Paragraph 62. A composition comprising: a sea salt and a sugar; wherein the sea salt and sugar have a mixed weight ratio from 1:1 to 1:30, wherein the weight of the sugar is equal to or greater than the weight of any other ingredient in the composition and wherein the total weight of the sugar and the sea salt is from 30% to 100% of the total weight of the composition.

Paragraph 63. The composition of Paragraph 62, wherein the sea salt is sodium chloride.

Paragraph 64. The composition of Paragraph 62, wherein the sugar is glucose.

Paragraph 65. The composition of Paragraph 62, wherein the composition is an insert preparation.

Paragraph 66. The composition of Paragraph 65, wherein the insert preparation is selected from the group consisting of a tablet, a capsule, a film, a sponge, a tampon, and a pad.

Paragraph 67. The composition of Paragraph 62, wherein the composition is a topical preparation.

Paragraph 68. The composition of Paragraph 67, wherein the topical preparation is selected from the group consisting of a cleansing liquid, a gel, a jelly, a foam, a cream, an ointment, a lotion, a balm, a patch, a paste, a spray solution and an aerosol.

Paragraph 69. The composition of Paragraph 62, further comprising dissolving the composition in a liquid at a percentage of the composition to the liquid from 0.01% to 99.99%.

Paragraph 70. The composition of Paragraph 69, wherein the percentage of the composition to the liquid is from 5% to 10%.

Paragraph 72. The composition of Paragraph 69, wherein the liquid is selected from the group consisting of distilled water, a buffered solution, an isotonic solution, a physiological saline, an oil, propylene glycol, ethanol and isopropyl myristate.

Paragraph 73. A method of treatment comprising a) administering to a mammal the composition of Paragraph 62; and b) placing the composition in a vagina of the mammal in need of treatment for a bacterial vaginosis infection, wherein the bacterial vaginosis infection is a *Gardnerella vaginalis* infection.

Paragraph 74. The method of Paragraph 73, wherein the treatment is selected from the group consisting of inhibition of development of the *Gardnerella vaginalis* infection, alleviation of the *Gardnerella vaginalis* infection and elimination of the *Gardnerella vaginalis* infection.

Paragraph 75. The method of Paragraph 73, wherein administering to the mammal comprises administering an amount of the composition in Paragraph 1 ranging from 0.001 mg to 1000 mg per kilogram of body weight of the mammal.

Paragraph 76. The method of Paragraph 75, wherein the amount of the composition in Paragraph 1 ranges from 0.01 mg to 100 mg per kilogram of body weight of the mammal.

Paragraph 77. The method of Paragraph 73, wherein the composition is administered from once a day to several times per day.

Paragraph 78. A composition consisting essentially of a combination of sodium chloride, glucose and a pharmaceutically acceptable carrier.

Paragraph 79. The method of Paragraph 78, wherein the composition is selected from the group consisting of a topical preparation and an insert preparation.

Paragraph 80. The method of Paragraph 79, wherein the topical preparation is selected from the group consisting of a cleansing liquid, a gel, a jelly, a foam, a cream, an ointment, a lotion, a balm, a patch, a paste, a spray solution and an aerosol.

Paragraph 81. The composition of Paragraph 80 wherein the composition is a cleansing liquid.

Paragraph 82. The method of Paragraph 79, wherein the insert preparation is selected from the group consisting of a tablet, a capsule, a film, a sponge, a tampon, and a pad.

Paragraph 83. The composition of Paragraph 82 wherein the composition is a tablet.

It will be apparent to those skilled in the art that various modifications and variations can be made in the compositions, use and preparations of the present disclosure without departing from the spirit or scope of the disclosure.

EXAMPLES

The following Examples and Experimental Examples are intended to further illustrate the present disclosure without limiting its scope.

Example 1

Preparation of the Combinations

Preparation of Melted Salt 900 mg of natural sea salt (Shinan, Korea) was melted for 24 hours at 850°-1000° C. using a heater (MS-E104, TOPS Co. Ltd.) to obtain 400 mg of the melted salt.

Preparation of Pure Salt 400 mg of pure salt (NaCl, F.W. 58.44) was procured from Duksan Co., Korea (SPPO-91701).

Preparation of Glucose 800 mg of glucose (crystalline glucose) was procured from Samyang Genex Corp., Korea.

Preparation of Combination (1)

400 mg of the melted salt and 800 mg of glucose prepared in the above steps, were thoroughly mixed together to obtain 1200 mg of the combination (designated as "SG1" hereinafter).

Preparation of Combination (2)

400 mg of the pure salt (sodium chloride) and 800 mg of glucose prepared in the above steps, were thoroughly mixed together to obtain 1200 mg of the combination (designated as "SG4" hereinafter).

The combinations were kept at −75° C. in a refrigerator and used in the following experiments by dissolving in distilled water before use.

Example 2

Preparation of Vaginal Tablet Composition

The combination prepared in Example 1 comprising 400 mg of melted salt and 800 mg of glucose was mixed with 2 mg of magnesium stearate in order to formulate the vaginal tablet composition combination (designated as "SG2" hereinafter) using an entableting apparatus (KT2000, Kumsung-kigong).

Example 3

Preparation of Vaginal Cleansing Solution Composition

The vaginal cleansing solution composition comprising the combination prepared in Example 1 comprising 400 mg of pure salt and 800 mg of glucose was prepared by mixing for 48 hours with stirring with the following ingredients as shown in Tablet 1 (designated as "SG3" hereinafter).

TABLE 1

| SG3 solution (100 ml) | | |
|---|---|---|
| Ingredient | | Amount |
| SG4 | | 0.5 g |
| Lactic acid | | 1 g |
| adjuvant | Whey | 180 mg |
| | Ethanol | 1 g |
| | Preservatives (benzalkonimum HCl and Trace amount menthol) | Trace amount |
| Distilled water | Appropriate amount to adjusted to 100 ml | |

Reference Example 1

Preparation & Reagent

Experimental Strains

For use in the following tests, two strains, (1) *Lactobacillus acidophilus* strain (KRIBB deposit No. KCTC 1120) and (2) *Gadnerella vaginalis* strain (KRIBB deposit No. KCTC 5096) were procured from KCTC (Korean Collection for Type Culture in KRIBB (Korea Research Institute of Bioscience & Biotechnology) and cultured in liquid medium (thioglycollate Medium, DIFCO™) at 37° C. or solid medium (blood agar plate) at 37° C. according to anaerobic pouch method (GasPak™, EZ Pouch System).

Materials

Combination (SG1) prepared in Example 1 was used as a test sample and lactic acid (Fluka Co., ACS reagent, 85-90%, L-lactic acid in water) was used in the experiment.

Experimental Example 1

Effect on the Growth of *Lactobacillus acidophilus*

To test the effect of the combination prepared in Example 1 on the growth of *Lactobacillus acidophilus*, the following test was performed according to the procedure disclosed in the literature (Choi, J. G. et al., Antibacterial activity of *Ecklonia cava* against methicillin-resistant *Staphylococcus aureus* and *Salmonella* spp., Foodborne Pathog. Dis., 2010 (April: 7(4), pp 435-441).

*Lactobacillus acidophilus* strain (KRIBB deposit No. KCTC 1120) was inoculated into a fresh blood agar plate and cultured in liquid medium (thioglycollate Medium, DIFCO™) at 37° C. at the concentration of $10^5$/ml and various concentrations of the test sample, i.e., 0 mg/ml (negative control), 0.001 mg/ml, 0.1 mg/ml and 10 mg/ml of SG1 and SG4 were treated thereto. The optical density (OD) value was determined using a photometer (Densimat, 50015-PONTE A EMA (F1); Biomerieux Italia S. P. A) in order to check the growth of the stain at 4, 8, 12 and 24 hours after the treatment.

The results can be seen in Table 2. The test sample groups treated with combination SG1 and SG4 showed an increasing effect on the production of lactic acid, which maintains the pH of the vaginal environment and the growth of *Lactobacillus acidophilus*.

TABLE 2

Effect on the growth of *Lactobacillus acidophilus*

| Sample | Conc. mg/ml | O.D. of *Lactobacillus acidophilus* | | | |
|---|---|---|---|---|---|
| | | 4 hrs. | 8 hrs. | 12 hrs. | 24 hrs. |
| CONTROL | 0 | 0.2 | 0.6 | 1.2 | 3.6 |
| SG1 | 0.001 | 0.2 | 0.6 | 1.2 | 3.9 |
| | 0.1 | 0.2 | 0.6 | 1.4 | 4.1 |
| | 10 | 0.2 | 0.7 | 1.5 | 4.3 |
| SG4 | 0.001 | 0.2 | 0.7 | 1.2 | 4.0 |
| | 0.1 | 0.2 | 0.8 | 1.5 | 4.2 |
| | 10 | 0.2 | 0.8 | 1.6 | 4.4 |

Experimental Example 2

Effect on the Growth of *Gadnerella vaginalis*

To test the effect of the combination prepared in Example 1 on the growth of *Gadnerella vaginalis*, a main cause of vaginosis, the following disk diffusion test was performed according to the procedure disclosed in the literature (Choi, J. G. et al., Antibacterial activity of *Hylomecon hylomeconoides* against methicillin-resistant *Staphylococcus aureus*, Appl. Biochem. Biotechnol., 2010 (April: 160(8), pp 2467-2474).

*Gadnerella vaginalis* strain (KRIBB deposit No. KCTC 5096) was inoculated into a fresh blood agar plate and cultured in 6 mm disk treated with 20 microliter of various concentrations of lactic acid, i.e., 0 μg/ml (Control), 0.2 μg/ml, 2 μg/ml, and 20 μg/ml of SG1 and SG4 for 24 hours. The inhibition distance (mm) of each disk was determined.

Vaginosis occurs by hyper-proliferation of anaerobic microbes caused by decreased growth of *Lactobacillus* spp. Accordingly, the treatment of lactic acid with *Gadnerella vaginalis* strains forms an effective inhibition zone in the disk. It is regarded that the production of lactic acid inhibited the growth of *Gadnerella vaginalis* strain, a main cause of vaginosis.

The results can be seen in Table 3. The test sample groups treated with the combinations SG1 and SG4 potently inhibited the growth of *Gadnerella vaginalis* strain in a dose dependent manner. Therefore, the combinations of SG1 and SG4 can be useful in treating or preventing vaginosis since they showed potent inhibitory effects on the growth of *Gadnerella vaginalis*.

TABLE 3

Effect on the growth of *Gadnerella vaginalis*
Treatment concentration of lactic acid with disk
(20 μl/disk)

| | Inhibition diameter (mm) | |
|---|---|---|
| Concentration | SG1 | SG4 |
| Control | 7 | 8 |
| 0.2 μg/ml | 10 | 12 |
| 2 μg/ml | 18 | 19 |
| 20 μg/ml | 25 | 28 |

Experimental Example 3

Brief Clinical Test (1)

1200 mg of the vaginal tablet composition (SG2) prepared in Example 2 was administrated intra-vaginally once a day for 5 days to 100 volunteers consisting of 35 patients suffering from vaginosis, and 65 normal women ranging from 20 to 50 years who live in Korea. A direct survey on the effects of the composition was performed.

The survey result on (A) the inhibition effect on unpleasant scent, (B) feeling of freshness and (C) alleviation effect on skin pruritus was classified into 4 categories, i.e., (1) very satisfied (2) satisfied, (3) common and (4) dissatisfied according to the intensity of each content. The results are shown in Table 4.

TABLE 4

| | Survey result | | | | |
|---|---|---|---|---|---|
| Content | Very satisfied | Satisfied | Common | Dissatisfied | Sum |
| A | 79 | 15 | 4 | 2 | 100 |
| B | 72 | 14 | 10 | 4 | 100 |
| C | 67 | 18 | 12 | 3 | 100 |

The results can be seen in Table 4. More than 94% of the people in the test group treated with combination SG2 were satisfied with (A) the inhibition effect on unpleasant scent, and more than 86% of the people in the test group treated with combination SG2 were satisfied with (B) the feeling of freshness. Furthermore, more than 85% of the people in the test group treated with combination SG2 were satisfied with (C) the alleviation effect on skin. Therefore, the combination SG2 can be useful in treating or preventing vaginosis.

Experimental Example 4

Brief Clinical Test (2)

200 ml of the vaginal cleansing composition (SG3) prepared in Example 3 was administrated externally once a day for 5 days to 100 volunteers consisting of 42 patients suffering from vaginosis, and 58 normal women ranging from 20 to 50 years who live in Korea. The difference of in the vaginal pH between the pH of (A) before and (B) after the treatment with the composition was determined using a pH meter from Yuyuinst Co., Korea (MP-103).

TABLE 5 pH difference

| SAMPLE | <3.5 | 4 | 4.5 | 5 | 5.5 | 6 | >6.5 | SUM |
|---|---|---|---|---|---|---|---|---|
| A | 0 | 2 | 7 | 9 | 17 | 49 | 16 | 100 |
| B | 4 | 27 | 37 | 21 | 9 | 2 | 0 | 100 |

The results can be seen in Table 5. The vaginal pH of 82% of the test group before the treatment with the composition was more than 5.5; however, 89% of the test group after the treatment with the composition reached a normal pH range.

Accordingly, it has been proved that the cleansing composition of SG3 can be useful in decreasing the vaginal pH of the patients suffering with vaginal alkalization.

A composition comprising a combination of salt and sugar showed potent antibacterial activity, especially *Gardnerella vaginalis*, a main cause of vaginosis, as well as, stimulating the production of lactic acid to maintain the vagina acidity by way of stimulating the proliferation of *Lactobacillus acidophilus*. Accordingly, the combination can be useful in treating or preventing vaginosis and useful in decreasing the vaginal pH of the patients suffering with vaginal alkalization.

The disclosure shows it is possible to vary the compositions in many ways. Such variations are not to be regarded as a departure from the spirit and scope of the present disclosure, and all such modifications as would be known to one skilled in the art are intended to be included within the scope of the following claims.

The invention claimed is:

1. A method of treatment comprising administering to a mammal in need of treatment for a bacterial vaginosis infection a composition, wherein the composition is placed in a vagina of the mammal and the composition comprises:
    melted sodium chloride and glucose;
    wherein the melted sodium chloride and the glucose are 20 to 99.99% by weight of the composition and wherein the weight ratio of melted sodium chloride to the glucose is 1:1-1:30, and wherein the bacterial vaginosis infection is a *Gardnerella vaginalis* infection.

2. The method of claim 1, wherein the composition further comprises a liquid selected from the group consisting of distilled water, a buffered solution, an isotonic solution, a physiological saline, an oil, propylene glycol, ethanol and isopropyl myristate.

3. The method of claim 1, wherein the treatment is selected from the group consisting of alleviation of the *Gardnerella vaginalis* infection and elimination of the *Gardnerella vaginalis* infection.

4. The method of claim 1, wherein administering to the mammal comprises administering an amount of the composition ranging from 0.001 mg to 1000 mg per kilogram of body weight of the mammal.

5. The method of claim 4, wherein the amount of the composition ranges from 0.01 mg to 100 mg per kilogram of body weight of the mammal.

6. The method of claim 1, wherein the composition is administered from once a day to several times per day.

7. The method of claim 1, wherein the composition further comprises a compound selected from the group consisting of an antibiotic, a dye, and a flavor at a concentration from 0.1% to 20% by weight of the composition.

8. The method of claim 1, wherein the composition is selected from the group consisting of a topical preparation and an insert preparation.

9. The method of claim 8, wherein the topical preparation is selected from the group consisting of a cleansing liquid, a gel, a jelly, a foam, a cream, an ointment, a lotion, a balm, a patch, a paste, a spray solution, and an aerosol.

10. The method of claim 9, wherein the topical preparation is a cleansing liquid.

11. The method of claim 8, wherein the insert preparation is selected from the group consisting of a tablet, a capsule, a film, a sponge, a tampon and pad.

12. The method of claim 11, wherein the insert preparation is a tablet.

13. A method of treatment comprising administering to a mammal in need of treatment for a bacterial vaginosis infection a composition, wherein the composition is placed in a vagina of the mammal and the composition comprises:
    melted Shinan sea salt and glucose;
    wherein the melted Shinan sea salt and the glucose are 20 to 99.99% by weight of the composition and wherein the weight ratio of melted Shinan sea salt to the glucose is 1:1-1:30, and wherein the bacterial vaginosis infection is a *Gardnerella vaginalis* infection.

14. The method of claim 13, wherein the composition further comprises a liquid selected from the group consisting of distilled water, a buffered solution, an isotonic solution, a physiological saline, an oil, propylene glycol, ethanol and isopropyl myristate.

15. The method of claim 13, wherein the treatment is selected from the group consisting of alleviation of the *Gardnerella vaginalis* infection and elimination of the *Gardnerella vaginalis* infection.

16. The method of claim 13, wherein administering to the mammal comprises administering an amount of the composition ranging from 0.001 mg to 1000 mg per kilogram of body weight of the mammal.

17. The method of claim 16, wherein the amount of the composition ranges from 0.01 mg to 100 mg per kilogram of body weight of the mammal.

18. The method of claim 13, wherein the composition is administered from once a day to several times per day.

19. The method of claim 13, wherein the composition further comprises a compound selected from the group consisting of an antibiotic, a dye, and a flavor at a concentration from 0.1% to 20% by weight of the composition.

20. The method of claim 13, wherein the composition is selected from the group consisting of a topical preparation and an insert preparation.

21. The method of claim 20, wherein the topical preparation is selected from the group consisting of a cleansing liquid, a gel, a jelly, a foam, a cream, an ointment, a lotion, a balm, a patch, a paste, a spray solution, and an aerosol.

22. The method of claim 21, wherein the topical preparation is a cleansing liquid.

23. The method of claim 20, wherein the insert preparation is selected from the group consisting of a tablet, a capsule, a film, a sponge, a tampon, and pad.

24. The method of claim 23, wherein the insert preparation is a tablet.

* * * * *